United States Patent
Higginbotham (10) Patent No.: US 11,058,842 B2
(45) Date of Patent: Jul. 13, 2021

(54) ADAPTER WITH MOISTURE TRAP ASSEMBLY FOR RESPIRATORY CIRCUIT

(71) Applicant: Pivotal Biotech LLC, Las Cruces, NM (US)

(72) Inventor: Brooke Higginbotham, Las Cruces, NM (US)

(73) Assignee: PIVOTAL BIOTECH LLC, Las Cruces, NM (US)

( * ) Notice: Subject to any disclaimer, the term of this patent is extended or adjusted under 35 U.S.C. 154(b) by 488 days.

(21) Appl. No.: 15/918,729

(22) Filed: Mar. 12, 2018

(65) Prior Publication Data

US 2018/0200469 A1  Jul. 19, 2018

Related U.S. Application Data (63) Continuation-in-part of application No. 15/243,575, filed on Aug. 22, 2016, now abandoned.
(Continued)

(51) Int. Cl.
*A61M 16/08* (2006.01)
*A61M 16/16* (2006.01)
(Continued)

(52) U.S. Cl.
CPC ........ *A61M 16/0808* (2013.01); *A61M 11/00* (2013.01); *A61M 16/14* (2013.01);
(Continued)

(58) Field of Classification Search
CPC ................ A61K 31/407; A61K 31/421; A61K 31/4965; A61K 31/65; A61K 38/482;
(Continued)

(56) References Cited

U.S. PATENT DOCUMENTS 2,757,672 A * 8/1956 Ogle ...................... A61M 5/347
                                                         604/241
4,090,513 A * 5/1978 Togawa ............ A61M 16/1045
                                                         128/201.13
(Continued)

FOREIGN PATENT DOCUMENTS

CN   203915713   11/2014
EP    0460731    3/1995
(Continued)

OTHER PUBLICATIONS http://www.teleflexarcatalog.com/anesthesia-respiratory/respiratory/categories/607, Heated Humidification Systems, 2 pages. Document was printed from the pertinent website on Aug. 31, 2016.
(Continued)

*Primary Examiner* — Annette Dixon
(74) *Attorney, Agent, or Firm* — Fernandez & Associates, LLP (57) ABSTRACT

Nebulizer systems, adapters, methods, and apparatuses are described for a nebulizer adapter that includes a body, an inlet for aerosolized respiratory medications, a breathing gas inlet tube and outlet tube, a barrier or body, and a drain lumen port that passes from the bottom of the barrier or body of the apparatus to the exterior into a port drain. The port drain would be in fluid communication with a receptacle removably attached to the annular lid that is attached to the bottom of the adapter body for collecting condensed moisture, wherein the receptacle comprise an actuator member configured to actuate the air tight seal of the annular lid upon attachment.

15 Claims, 3 Drawing Sheets

Related U.S. Application Data (60) Provisional application No. 62/208,718, filed on Aug. 23, 2015, provisional application No. 62/471,360, filed on Mar. 14, 2017.

(51) Int. Cl.
*A61M 16/14* (2006.01)
*A61M 11/00* (2006.01)

(52) U.S. Cl.
CPC ........... *A61M 16/16* (2013.01); *A61M 11/003* (2014.02); *A61M 11/005* (2013.01); *A61M 16/0816* (2013.01); *A61M 16/0875* (2013.01)

(58) Field of Classification Search
CPC .... A61K 45/06; A61K 9/0075; A61K 9/0078; A61K 9/12; A61K 9/14; A61M 11/00; A61M 11/001; A61M 11/002; A61M 11/003; A61M 11/005; A61M 11/02; A61M 11/04; A61M 11/041; A61M 11/06; A61M 15/0016; A61M 15/0085; A61M 15/0086; A61M 15/025; A61M 16/00; A61M 16/0808; A61M 16/0816; A61M 16/0833; A61M 16/0875; A61M 16/1055; A61M 16/1075; A61M 16/108; A61M 16/1085; A61M 2202/0275; A61M 2205/33; A61M 2205/36; A61M 2205/366; A61M 2205/52; A61M 2205/75; A61M 2205/7518; A61M 2205/7536; A61M 2206/14; A61M 2206/16; A61M 39/105; A61M 5/347; A61M 16/0057; A61M 16/06; A61M 16/0666; A61M 16/0672; A61M 16/08; A61M 16/1095; A61M 16/12; A61M 16/14; A61M 16/147; A61M 16/16; A61M 16/208; A61M 2039/1072; A61M 2202/0007; A61M 2202/0208; A61P 11/00; A61P 31/04; A61P 31/10; A61P 31/12; A61P 31/14; A61P 31/22; A61P 43/00; A61P 11/02; A61P 11/06; A61P 11/08; A61P 11/12; A61P 29/00; B05B 12/081; B05B 17/0646; B05B 17/0669; C12N 15/113; C12N 2310/14; C12Y 304/21075; Y02A 50/385; Y10S 128/912
See application file for complete search history.

(56) References Cited

U.S. PATENT DOCUMENTS

| | | | | |
|---|---|---|---|---|
| 4,417,574 A * | 11/1983 | Talonn | ............... | A61M 16/0808 128/205.12 |
| 4,457,305 A | 7/1984 | Shanks et al. | | |
| 4,951,661 A * | 8/1990 | Sladek | ............... | A61M 16/0808 128/202.27 |
| 5,119,807 A * | 6/1992 | Roberts | ................. | A61M 16/16 128/200.21 |
| 5,131,387 A * | 7/1992 | French | ................... | A61B 5/097 128/205.12 |
| 5,203,353 A | 4/1993 | Easley et al. | | |
| 5,228,436 A | 7/1993 | Parkin | | |
| 5,388,571 A * | 2/1995 | Roberts | ................. | A61M 16/16 128/200.18 |
| 5,398,677 A * | 3/1995 | Smith | ............... | A61M 16/0808 128/205.12 |
| 7,383,852 B2 | 6/2008 | Pittaway et al. | | |
| 8,210,177 B2 | 7/2012 | Payne et al. | | |
| 8,215,304 B2 | 7/2012 | Reinboth et al. | | |
| 8,678,355 B2 | 3/2014 | Steg et al. | | |
| 8,714,155 B2 | 5/2014 | Hsiao | | |
| 2003/0024528 A1 * | 2/2003 | Graham | ............... | A61M 16/106 128/201.13 |
| 2003/0127094 A1 * | 7/2003 | Roberts | ............. | A61M 16/0666 128/203.22 |
| 2006/0042636 A1 * | 3/2006 | Nalagatla | .......... | A61M 16/0808 128/207.18 |
| 2006/0243274 A1 * | 11/2006 | Lieberman | ........ | A61M 15/0085 128/200.14 |
| 2007/0283951 A1 * | 12/2007 | Burk | ..................... | A61M 16/06 128/200.21 |
| 2008/0027344 A1 * | 1/2008 | Terry | ................. | A61M 16/0666 600/532 |
| 2010/0089395 A1 * | 4/2010 | Power | ............... | A61M 16/0672 128/203.15 |
| 2010/0258114 A1 * | 10/2010 | Cortez, Jr. | ........... | A61M 11/005 128/200.23 |
| 2012/0138058 A1 * | 6/2012 | Fu | ..................... | A61M 16/0066 128/204.23 |
| 2013/0074842 A1 * | 3/2013 | Boucher | ................. | A61P 11/06 128/203.16 |
| 2014/0109899 A1 * | 4/2014 | Boucher | .............. | A61K 31/421 128/200.18 |
| 2014/0150794 A1 | 6/2014 | Kendrick et al. | | |
| 2015/0352299 A1 * | 12/2015 | Cortez, Jr. | ............. | A61M 11/06 128/200.23 |
| 2017/0246417 A1 * | 8/2017 | Kemps | ............. | A61M 16/0069 |
| 2018/0200469 A1 | 7/2018 | Higginbotham | | |

FOREIGN PATENT DOCUMENTS

| | | |
|---|---|---|
| JP | 2012232067 | 11/2012 |
| WO | 2014027290 | 2/2014 |

OTHER PUBLICATIONS httpx//www.alibaba.com/product-detail/PP-material-water-trap-for-breathing_60435565580.html?spm=a2700.7724857.0.0.tLRcLx&s=p, PP Material Water Trap for Breathing Circuit, 4 pages. Document was printed from the pertinent website on Aug. 31, 2016.

http://www.ventureresp.com/product/pc/viewPrd.asp?dproduct=1704&idcategory=, CareFusion Self-sealing Water Trap, 50/cs (001860), 5 pages. Document was printed from pertinent website on Aug. 31, 2016.

http://nbaya.en.alibaba.com/product/914855428-218874795/100_PP_Y_Connector_Medical.html, 100% PP Y Connector Medical, 5 pages. Document was printed from pertinent website on Aug. 31, 2016.

http://tenhoo.en.hisupplier.com/product-583863-Water-CUP.html, Water Cup, 6 pages. Document was printed from pertinent website on Aug. 31, 2016.

http://nbaya.en.alibaba.com/product/958214316-218874795/T_Shaped_connector_for_nebulizer_kit.html, T Shaped connector for nebulizer kit, 6 pages. Document was printed from pertinent website on Aug. 31, 2016.

http://www.iiimedical.com/proddetail.php?prod=PS54AI, PS 54AL Low Resistance Exhalation Valve/Water Trap Assembly, 3 pages. Document was printed from pertinent website on Aug. 31, 2016.

\* cited by examiner

ADAPTER WITH MOISTURE TRAP ASSEMBLY FOR RESPIRATORY CIRCUIT

CROSS REFERENCE TO RELATED APPLICATIONS

This application is a continuation-in-part from U.S. patent application Ser. No. 15/243,575, filed on Aug. 22, 2016, which claims the benefit of U.S. Provisional Application Ser. No. 62/208,718, filed on Aug. 23, 2015, now abandoned; the entirety of each disclosure is incorporated herein by reference.

This application claims the benefit of U.S. Provisional Application Ser. No. 62/471,360, filed on Mar. 13, 2017; the disclosure of which is incorporated herein by reference.

BACKGROUND

The present disclosure relates to a medical utility device for use with respiratory airline apparatus including Vapotherm®, and more particularly relates to a nebulizer adapter that allows the passage of gas, that includes a drainage port that allows for the passage of moisture or water vapor that flows into a evaporative dispersal system for capturing moisture from the respiratory air or breathing gas passing through the respiratory circuit and nebulizer adapter.

People with respiratory ailments, including but not limited to general respiratory distress, RSV (respiratory syncytial virus), CHF (congestive heart failure), asthma, pneumonia, COPD (chronic obstructive pulmonary disorder) and patients in neonate care, adult intensive care, sub-acute care, palliative care, who are in need of high flow therapy (HFT) medical apparatuses that allows for the delivery of high flow pressure rate of breathing gases to the patient, in order to effectively provide an increase of fraction of inspired oxygen along with the decreasing the rate of the patients work of breathing, to prevent intubation or to help aid with normal breathing process, may utilize respiratory circuit or respiratory airline systems such as Vapotherm®, apparatus.

Respiratory airline apparatus such as HFT are widely used apparatuses in the medical field for facilitating patients' breathing by providing a continuous supply of clean breathing gas, such as oxygen or other needed gases or a combination of gases. In addition, the breathing system is usually used in combination with a humidifier in order to adjust the humidity of the breathing gas according patient's body temperature thereby raising the comfort level during breathing. Further, the breathing system is also capable of dosing respiratory medication to further augment the patient's breathing circulation. Patients receiving medications, may need the use of a nebulizer that allows for aerosolized respiratory medications such as bronchodilators, salbutamol, and levosalbutamol/Levalbuterol for treating the correlating ailments such as asthma or COPD. Nebulizer adapter devices may be connected to HFT and other respiratory devices to provide an inlet and aerosolized medicated chamber to administer such medications while providing continuous gas flow to the patient. This nebulizer adapter with moisture trap connects to a wide range of nebulizers including but not limited to the Aeroneb® nebulizer.

In a low temperature environment, the breathing gas and/or patient's exhaled breath in the respiratory circuit tends to condense inside the circuit, adapter, or cannula of the breathing system. Thus, several liquid trap assemblies are normally provided to collect the waste liquid accumulated in the circuit. This nebulizer adapter provides for a liquid trap to remove the condensate from the breathing system. Condensation in a the breathing system presents both clinical and mechanical impediments as the condensate can limit flow through the system, can negate the percentage of aerosolized medication administered to the patient, and can accumulate bacteria or other materials that can become a biological risk to the patient. The waste liquid in the nebulizer adapter liquid trap assemblies must be drained regularly in order to properly maintain the function of the breathing system, and to prevent microbial contamination.

Comparable incidents regarding the condensation and accumulation of water caused by the Vapotherm®, apparatus, were noted by healthcare professionals nationwide and to the United States Food and Drug Administration (FDA). According to recent events reported by the United States Food and Drug Administration (FDA), the breathing system including the circuit to adapter to cannula of the Vapotherm®, HFT was accumulating water at an average rate of 3 milliliters/hour; this rate is comparable to that of the accumulation of water that was observed in the healthcare facilities. This versatile nebulizer adapter with moisture trap apparatus will pass the condensate through the drainage port into the moisture trap receptacle that will capture the condensate at an equal to or greater than rate of that calculated by the FDA, hospital reports, and collected data. This allows one moisture trap collection cup to accumulate water with ample time for the hospital staff to dispense the condensate from the removable and disposable moisture collection receptacle. This versatile nebulizer adapter allows for the removal of unwanted condensate and the use of continuous gas flow with medication to the patient.

Accumulation of moisture or water vapor result in water accumulation or "Raining out" and water flowing into the patients' nostrils. Without the implementation of a versatile nebulizer with moisture trap apparatus, accumulation of water forms within the aerosol adapter or other medication adapter and nebulizer adapters, causing a significant degree of rain-out formation.

Prior art related to moisture trap apparatuses comprises limitations including inability to connect accurately with the input and output lines of the respiratory circuit such as the Vapotherm®, Inc. adapter provided in U.S. PG Pub. 2015/0352299. Another limitation includes obstruction to the flow of oxygen, heliox or precision air due to frequent disconnection of the respiratory circuit system from the aerosol adapter, which results in both water leakage, medication and gas flow obstruction. During the time of disconnect, the patient in not receiving high flow therapy or medication. Therefore, existing moisture trap apparatuses do not effectively solve the problem of water accumulation, efficient medication delivery and continuous air flow in high flow apparatus.

SUMMARY

Issues continue to exist with existing adapters for nebulizers since they do not solve the water accumulation problem. The present disclosure addresses these and other issues by providing an adapter for airline circuitry or an airline circuit that can drain fluid condensate that results from warmed and humid breathing air mixing with nebulized medicine inside a mixing chamber.

In another aspect, an exemplary embodiment of the present disclosure may provide an adapter for a respiratory line comprising: a body that defines a first inlet, a second inlet, and an outlet, wherein the first inlet is associated with only a single lumen that fluidly receives breathing gas therethrough and the second inlet receives and connects with a nebulizer; an exterior surface of the body and an interior surface of the body; a mixing chamber defined by the interior surface of the body, wherein medicine from the nebulizer mixes with the breathing gas inside the mixing chamber and collective flow outwardly from the body through the outlet; and a drainage port formed in the body in fluid communication with the mixing chamber to drain fluids that condense on the interior surface when the gas and medicine are mixed in the mixing chamber. This embodiment or another exemplary embodiment may further provide a lid connected to the body below the drainage port. This embodiment or another exemplary embodiment may further provide a receptacle removably attached to the lid for collecting fluids flowing out from the mixing chamber through the drainage port. This embodiment or another exemplary embodiment may further provide a uniform and non-hollow thickness of the body between the exterior surface and the interior surface to effectuate the adapter as a single lumen adapter and not a first inlet double lumen adapter. This embodiment or another exemplary embodiment may further provide a screen between the second inlet and the mixing chamber. This embodiment or another exemplary embodiment may further provide wherein the screen is defined by holes formed in a wall of the body between the mixing chamber and the second inlet. This embodiment or another exemplary embodiment may further provide threads on the lid that removably attach the receptacle; and a seal covering drainage port that is opened in response to the receptacle being threadedly attached to the lid to permit fluid to drain from the mixing chamber through the drainage port and into the receptacle. This embodiment or another exemplary embodiment may further provide an annular sidewall on the lid extending downwardly from a circular wall integrally formed with the exterior surface of the body; wherein the annular sidewall is positioned below the mixing chamber and below the second inlet that receives the nebulizer. This embodiment or another exemplary embodiment may further provide an actuation member carried by receptacle that closes a seal for the drainage port when the receptacle is detached from the lid. This embodiment or another exemplary embodiment may further provide wherein the lid is shaped and formed in a bottle cap configuration. This embodiment or another exemplary embodiment may further provide an imaginary vertical axis extending through the body; and a center of the drainage port aligned along the imaginary vertical axis below the second inlet. This embodiment or another exemplary embodiment may further provide a downwardly tapered collar defining a portion of the interior surface of the body in the mixing chamber adjacent the drainage port configured to promote fluid accumulating near the bottom of the mixing chamber to flow outwardly through the drainage port. This embodiment or another exemplary embodiment may further provide an annular sidewall on a lid extending downwardly from a rigid connection adjacent the exterior surface of the body; a center of the annular sidewall aligned along the imaginary vertical axis; and a diameter of the annular sidewall that is greater than a diameter of the second inlet. This embodiment or another exemplary embodiment may further provide a vertically aligned length of the annular sidewall that is less than the diameter of the annular sidewall. This embodiment or another exemplary embodiment may further provide a vertically aligned length of the annular sidewall that is less than a vertically aligned length of the second inlet. This embodiment or another exemplary embodiment may further provide threads extending radially inward towards the imaginary vertical axis from an inner surface of the annular sidewall; and complementary threads on a receptacle effectuating the removable attachment between the lid and the receptacle.

The present disclosure relates to a versatile nebulizer with moisture trap assembly for a respiratory circuit, comprising: 1) a flow connector unit comprising: a body that allows for gas to flow from an inlet tube in fluid connection with an outlet tube and a drain lumen that passes from the bottom of the body to the exterior into a drainage port, wherein the inlet and outlet tubes are adapted to fit to the respiratory circuit; and 2) a receptacle removably attached to the annular lid that is attached to the bottom of the body for collecting water accumulated from trapped moisture; 3) an actuator member attached to a removable moisture collection cup or other removable moisture collection receptacle.

In yet another aspect, an exemplary embodiment of the present disclosure may provide nebulizer systems, adapters, methods, and apparatuses are described for a nebulizer adapter that includes a body, an inlet for aerosolized respiratory medications, a breathing gas inlet tube and outlet tube, a barrier or body, and a drain lumen port that passes from the bottom of the barrier or body of the apparatus to the exterior into a port drain. The port drain may be in fluid communication with a receptacle removably attached to the annular lid that is attached to the bottom of the adapter body for collecting condensed moisture, wherein the receptacle comprise an actuator member configured to actuate the air tight seal of the annular lid upon attachment.

In yet another aspect, an exemplary embodiment of the present disclosure may provide a moisture trap assembly for a respiratory circuit, comprising: a flow connector unit comprising a body that allows for gas to flow from an inlet tube in fluid connection with an outlet tube and a drainage port that passes through a bottom of the body to the exterior thereof, wherein the inlet and outlet tubes are adapted to fit to the respiratory circuit; and an actuator member attached to a removable receptacle.

In yet another aspect, an exemplary embodiment of the present disclosure may provide an adapter for a respiratory line comprising: a body that has a first end and a second end defining a longitudinal direction therebetween, a top and a bottom defining a vertical direction therebetween, and a first side and a second side defining a transverse direction therebetween, and the body defines a first inlet, a second inlet, and an outlet, wherein the first inlet is associated with only a single lumen that fluidly receives warned and humidified breathing gas therethrough and the second inlet receives and connects with a nebulizer; a central vertical axis and a central longitudinal axis, wherein the first inlet and the outlet are centered along the longitudinal axis; a convex exterior surface of the body and a concave interior surface of the body; a uniform and non-hollow thickness of the body between the exterior surface and the interior surface to effectuate the adapter as a single lumen adapter and not a first inlet double lumen adapter; a cylindrical wall on the body having a length oriented in the longitudinal direction that is greater than its diameter oriented in the vertical direction; a first tapered collar connected to one end of the cylindrical wall on the body, wherein the first tapered collar is angled downwardly towards the longitudinal axis; a second tapered collar connected to another end of the cylindrical wall on the body, wherein the second tapered collar is angled downwardly towards the longitudinal axis in a direction opposite that of the first tapered collar, and wherein the second tapered collar is angled at a steeper angle relative to the longitudinal axis than the first tapered collar; a first cylindrical extension connected with the first tapered collar defining a portion of the first inlet, and the first cylindrical extension having a diameter less than that of the cylindrical wall on the body; a second cylindrical extension connected with the second tapered collar defining a portion of the outlet, and the second cylindrical extension having a diameter less than that of the cylindrical wall on the body and less than that of the first cylindrical extension; a mixing chamber defined by the concave interior surface of the body, wherein medicine from the nebulizer mixes with the breathing gas inside the mixing chamber and collective flow outwardly from the body through the outlet along a tube connected with the outlet for inhalation by a patient; a screen between the second inlet and the mixing chamber, wherein the screen is defined by a plurality of holes formed in the cylindrical wall of the body between the mixing chamber and the second inlet; an axis of the second inlet angled in a range from about 15° to about 75° relative to the vertical axis, and wherein a portion of the nebulizer is oriented at a similar angle as the second inlet relative the central axis; a drainage port formed in near a the bottom of the body in fluid communication with the mixing chamber to drain fluids that condense on the interior surface when the warmed and humidified breathing gas and medicine are mixed in the mixing chamber, wherein the drainage port is centered along the vertical axis; a downwardly sloping wall defining a portion of the interior surface of the body in the mixing chamber adjacent the drainage port configured to promote fluid accumulating near the bottom of the mixing chamber to flow outwardly through the drainage port; a lid connected to the body below the drainage port and centered along the vertical axis, and the lid comprising an annular sidewall extending downwardly from a circular wall integrally formed with the exterior surface of the body and threads on an inner surface of the annular sidewall, wherein the annular sidewall is positioned below the mixing chamber and below the second inlet that receives the nebulizer; a diameter of the annular sidewall that is greater than a diameter of the cylindrical wall on the body; and a receptacle removably attached to the lid for collecting fluids flowing out from the mixing chamber through the drainage port and complementary threads on a receptacle effectuating the removable attachment between the lid and the receptacle.

BRIEF DESCRIPTION OF THE SEVERAL VIEWS OF THE DRAWINGS

A sample embodiment of the disclosure is set forth in the following description, is shown in the drawings and is particularly and distinctly pointed out and set forth in the appended claims. The accompanying drawings, which are fully incorporated herein and constitute a part of the specification, illustrate various examples, methods, and other example embodiments of various aspects of the disclosure. It will be appreciated that the illustrated element boundaries (e.g., boxes, groups of boxes, or other shapes) in the figures represent one example of the boundaries. One of ordinary skill in the art will appreciate that in some examples one element may be designed as multiple elements or that multiple elements may be designed as one element. In some examples, an element shown as an internal component of another element may be implemented as an external component and vice versa. Furthermore, elements may not be drawn to scale.

FIG. 1 is a first side elevation view of an adapter for a nebulizer having a drainage receptacle in accordance with the present disclosure.

FIG. 2 is a top plan view of the adapter.

FIG. 3 is a vertical cross-section view of the adapter taken along line 3-3 in FIG. 1.

FIG. 4 is a longitudinal cross-section view of the adapter taken along line 404 in FIG. 4.

FIG. 5 is a longitudinal cross-section view of the adapter connected to breathing airline circuitry and a nebulizer depicting fluid condensate collecting into a receptacle.

Similar numbers refer to similar parts throughout the drawings.

DETAILED DESCRIPTION

Initially, the Inventors/Applicant note that the present disclosure is a continuation-in-part of U.S. patent application Ser. No. 15/243,575 (the '575 Application) filed on Aug. 22, 2106, which claims the benefit of U.S. Provisional Patent Application Ser. No. 62/208,718 (the '718 Application) filed on Jul. Aug. 23, 2015, now abandoned, and the present disclosure claims the benefit of U.S. Provisional Patent Application Ser. No. 62/471,360 (the '360 Application) filed on Mar. 13, 2017, the entirety of each is fully incorporated herein as if fully re-written. The present disclosure touches upon additional subject matter to the aforementioned '575 Application, '718 Application, and '360 Application, namely, adapters for airline circuitry that connect with a nebulizer and have a drainage port to allow fluids to drain from the mixing chamber. Since this is a continuation-in-part application of the '575 Application, some similar structural nomenclature is used herein when referencing some portions of the adapter. However, there may be some instances where structural nomenclature differs between similar elements and there may be other instances where nomenclature is similar between distinct elements relative to this application and the '575 Application, the '718 Application, and the '360 Application. The terms used in this disclosure apply to this disclosure and may not necessarily apply to other applications or issued patents in this family. Further in this regard, terms used in the specification(s) of the '575 Application, the '718 Application, and the '360 Application may or may not necessarily apply to this disclosure.

An adapter, which may also be referred to herein or in other related applications as a flow connecter unit, is shown generally throughout the figures at 10. The adapter 10 is configured to define a moisture trap assembly 12 (FIG. 5) when a receptacle 14 is attached to the adapter 10. As depicted in FIG. 1, the adapter 10 includes a first end 16 opposite a second end 18 defining a longitudinal direction therebetween, a top 20 opposite a bottom 22 defining a vertical direction therebetween, and a first side 24 (FIG. 2) opposite a second side 26 (FIG. 2) defining a transverse direction therebetween.

Adapter 10 includes a body 28 that may be formed from a plurality of components connected together or may be integrally formed as one molded piece of material. In one particular embodiment, body 28 is fabricated from polymers that are sufficiently strong yet also light-weight and may include antimicrobial properties. For example, the adapter may be molded in as a single piece mold such that the body is substantially a unibody, monolithic member formed from a uniform material.

The body 28 of adapter 10 defines a first inlet 30, a second inlet 32, an outlet 34, and a drainage port 36 (FIG. 4). The body 28 is a substantially cylindrical member extending longitudinally from the first end 16 towards the second end 18 and is centered about a longitudinal axis 38 (FIG. 4). The generally cylindrical body 28 may include a body cylindrical wall 40 of outer surface 42 extending between the first inlet 30 and the outlet 34 centered about the longitudinal axis 38. The body cylindrical wall 40 of the body 28 may include a convex outer surface 42 opposite a concave inner surface 44. The length of the cylindrical body may be on the order of a few inches. In one particular embodiment, the cylindrical wall is in a range from about one inch to about four inches. Further the length of the body cylindrical wall 40 is oriented along the longitudinal axis has a larger dimension than the diameter of the body cylindrical wall 40 which is oriented in the vertical direction. In some instances, the length of the body cylindrical wall 40 is at least twice that of the diameter of the body cylindrical wall 40.

Figure 4:
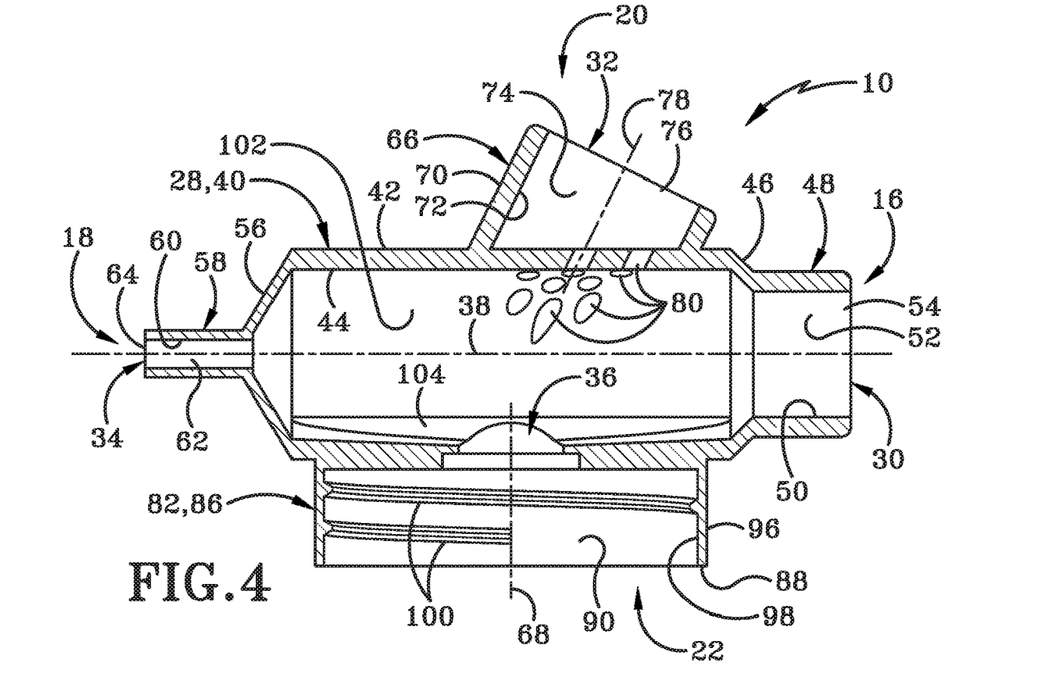
Figure 5:
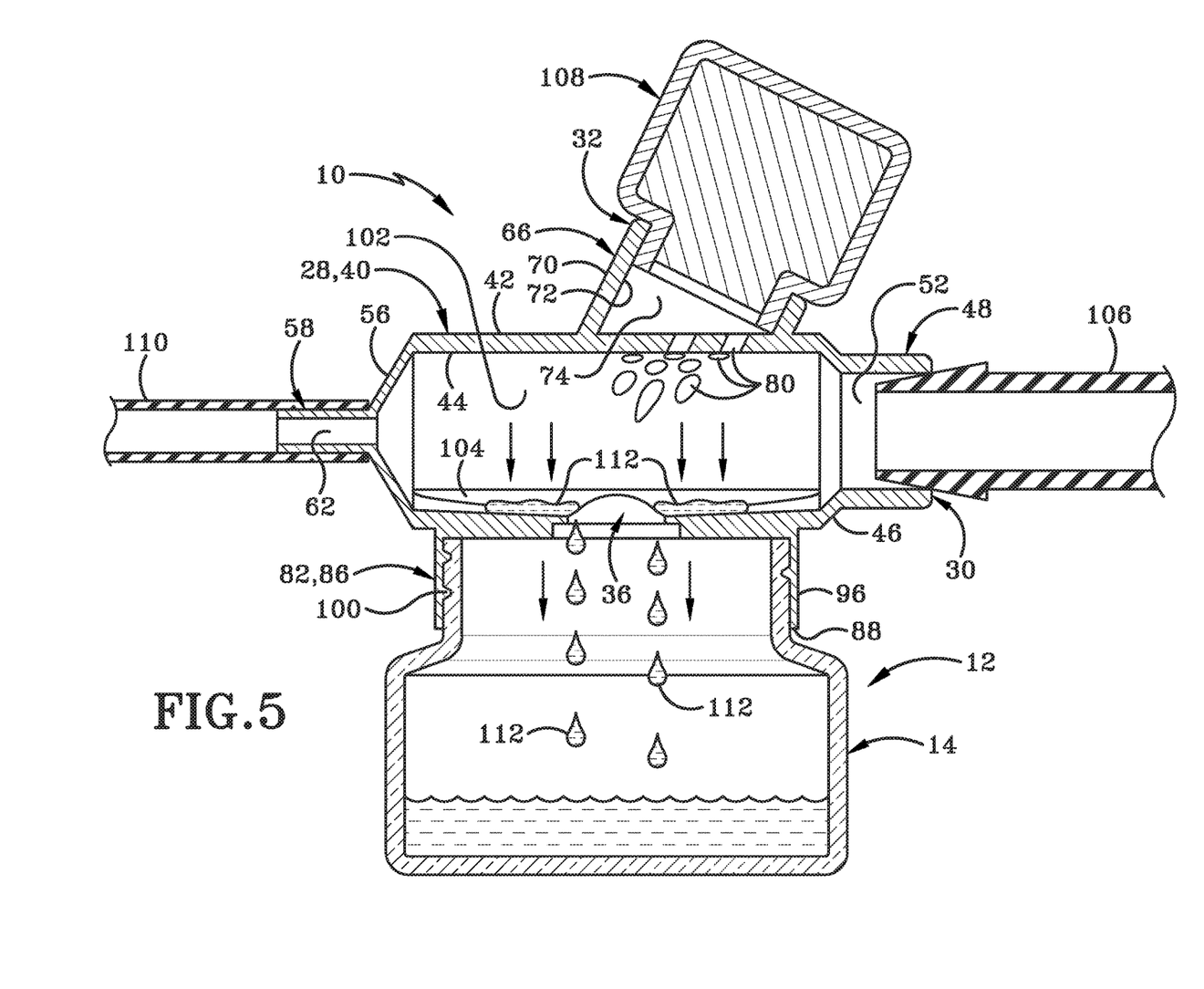

The body 28 has substantially uniform in thickness between the outer surface 42 and the inner surface 44. In one particular embodiment, the body 28 is solid and not hollow between the outer surface 42 and the inner surface 44. Stated otherwise, the body 28 does not form a lumen or other vacuum or space in which fluids or gases may flow between the inner surface 44 and the outer surface 42 in a circumferential manner around either the longitudinal axis 38 or the central vertical axis 68 (FIG. 4).

The body 28 further includes a first tapered collar 46 connected with the body cylindrical sidewall 40. The tapered collar 46 tapers radially inward towards the longitudinal axis 38 and is connected with a cylindrical extension 48 associated with the first end 16 of the adapter 10 and defines the first inlet 30. The cylindrical extension 48 includes an inner surface 50 that defines a lumen or passageway 52 in open communication with an opening 54 for the first inlet 30. The dimensions of the first inlet 30 and outlet 34 are sized to snugly fit with tubing of a respiratory circuit from a HFO apparatus or other breathing apparatus and output of a cannula, respectively. The cylindrical extension has an outer diameter that is smaller than the outer diameter of the body cylindrical sidewall 40. The cylindrical extension has an inner diameter that is smaller than an inner diameter of the body cylindrical wall 40.

Adjacent the second end 18, the body 28 further includes a second tapered collar 56 that tapers downwardly towards the longitudinal axis 38 to a second cylindrical extension 58 associated with the second end 18 and defining the outlet 34. Second tapered collar 56 tapers at an angle steeper than tapered collar 46 relative to the longitudinal axis 38. In one particular embodiment, the angle in which the tapered collar 56 tapers or is angled or intersects the longitudinal axis 38 is in a range between 90° and 45°. The second cylindrical extension 58 includes an inner surface 60 defining an outlet passageway 62 in fluid communication with an outlet opening 64 for the outlet 34. The passageway 62 is centered about the longitudinal axis 38. The outer diameter of the second cylindrical extension 58 is less than that of the first cylindrical extension 48. The inner diameter of the second cylindrical extension 58 is less than that of the first cylindrical extension 48. In one particular embodiment the diameters of the second cylindrical extension 58 are no more than half those of the first cylindrical extension 48. Stated otherwise, the ratio of the outer diameter of the second cylindrical extension relative to the outer diameter of the first cylindrical extension is at most about 0.5:1. However, clearly other dimensional and ratios are entirely possible.

The body 28 that defines the second inlet 32 further includes an outer cylindrical wall 66 that extends and is angled upwardly and towards the first side relative to a vertical axis 68. The outer cylindrical wall 66 includes a convex outer surface 70 opposite a concave inner surface 72 defining a passageway 74 in open communication with an opening 76 of the second inlet 32. The cylindrical wall 66 associated with the second inlet 32 is centered about an axis 78 that is non-orthogonally angled relative to the longitudinal axis 38 and the vertical axis 68. More particularly, the axis 78 associated with the second inlet 32 is non-orthogonal to the longitudinal axis 38 and is non-orthogonal to the vertical axis 68. In one particular embodiment, the angle defined between the longitudinal axis 38 and the axis 78 of the second inlet 32 is in the range from about 20° degree to about 80° degree. In one particular embodiment, the angle may be in a range from about 45 degree to about 70 degree. In one specific example, the angle defined between the axis 78 of the second inlet 32 is about 60.degree. An angle is formed between the axis 78 of the second inlet 32 and the central vertical axis 68 associated with the adapter 10. The angle in one particular embodiment between axis 78 and axis 68 is about 30.degree. However, it may be in a range from about 15.degree. to about 75.degree. depending on the orientation and desired size of a device, such as a nebulizer configured to be connected with the second inlet 32. As will be described below, the orientation of the second inlet 32 causes and external device, such as a nebulizer 108, that is connected with the second inlet to be canted or angled in a similar manner. Thus, a central axis associated with a portion of the nebulizer 108 would be oriented at an angle in a range from about 45.degree. to about 70.degree. relative to the longitudinal axis 38 and oriented at an angle in a range from about 15.degree. to about 75.degree. relative to the central vertical axis 68.

Figure 1:
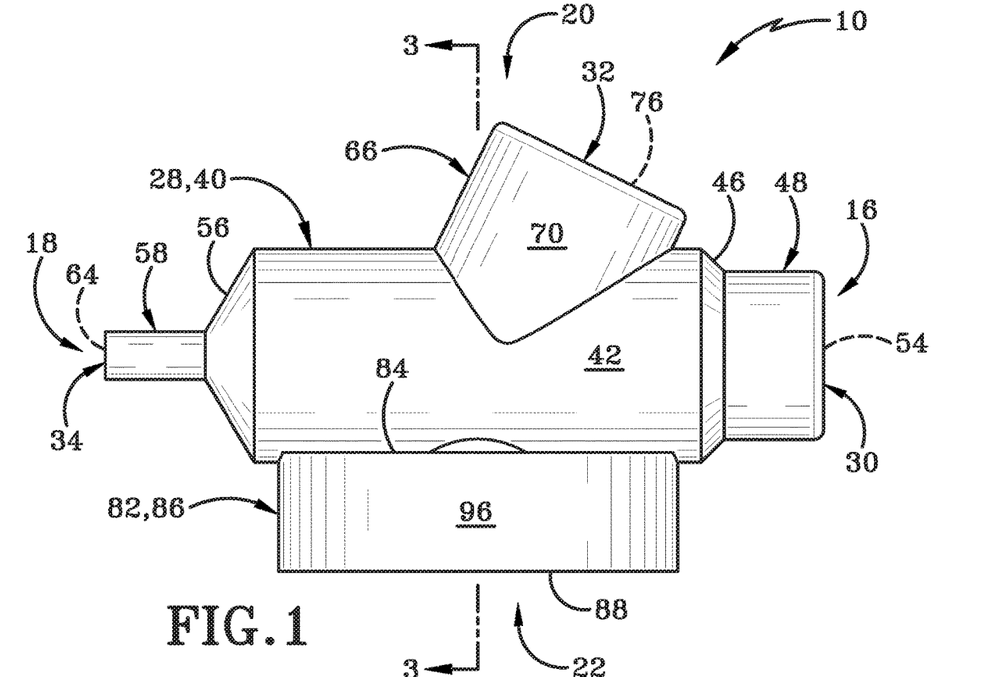
Figure 2:
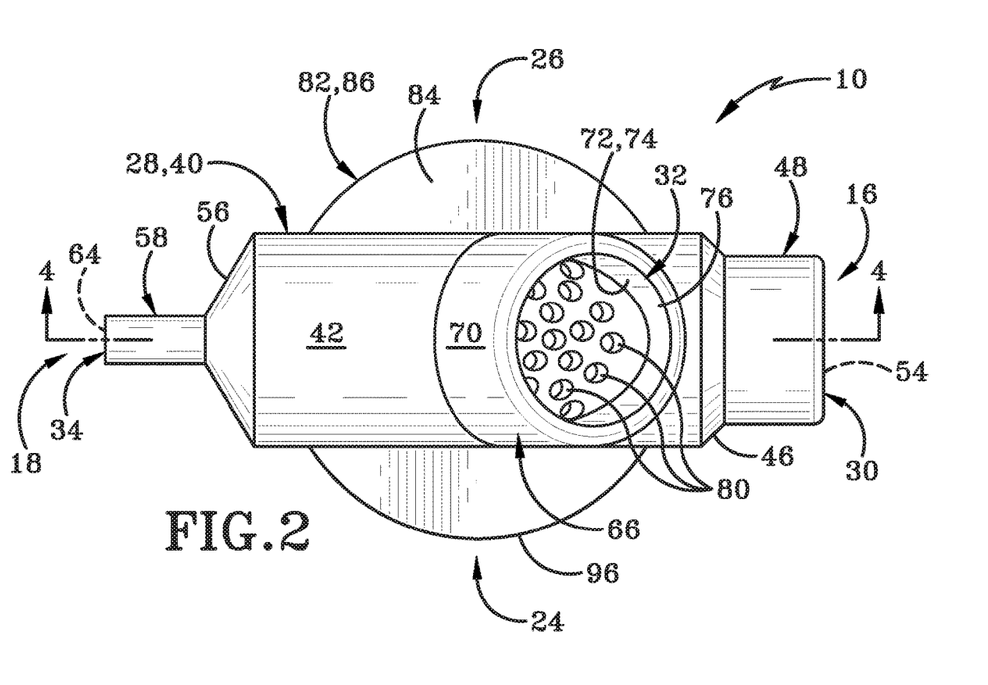

As depicted in FIG. 2, a plurality of holes 80 are formed in the body cylindrical wall 40 of the body 28. The holes 80 extend at least partially circumferentially around the longitudinal axis 38 in the body cylindrical wall 40. In one particular embodiment, the holes 80 are only formed in the portion of the body cylindrical wall 40 that effectuate fluid communication between the passageway 74 of the second inlet 32 with the interior of the body 28. Remarkably, the holes 80 do not affect the cylindrical body 28 from remaining substantially solid and non-hollow. The holes may form a geometric pattern or they may be randomly positioned throughout the body cylindrical wall 40 below the second inlet 32. In one particular embodiment, each one of the plurality of holes 80 is angled at a similar angle as the axis 78. Stated otherwise, as seen in FIG. 4, the center of the axis 78 remains uniformly centered along the length of each one of the holes 80 relative to the cylindrical wall 66 associated with the second inlet 32. Collectively, the plurality of holes 80 define a mesh or a screen that is configured to allow fluid movement therethrough extending fully through the body cylindrical wall 40 from its outer surface 42 into its inner surface 44. The holes do not permit a volume of fluid to be retained and bound between the outer surface 42 and the inner surface 44.

Figure 3:
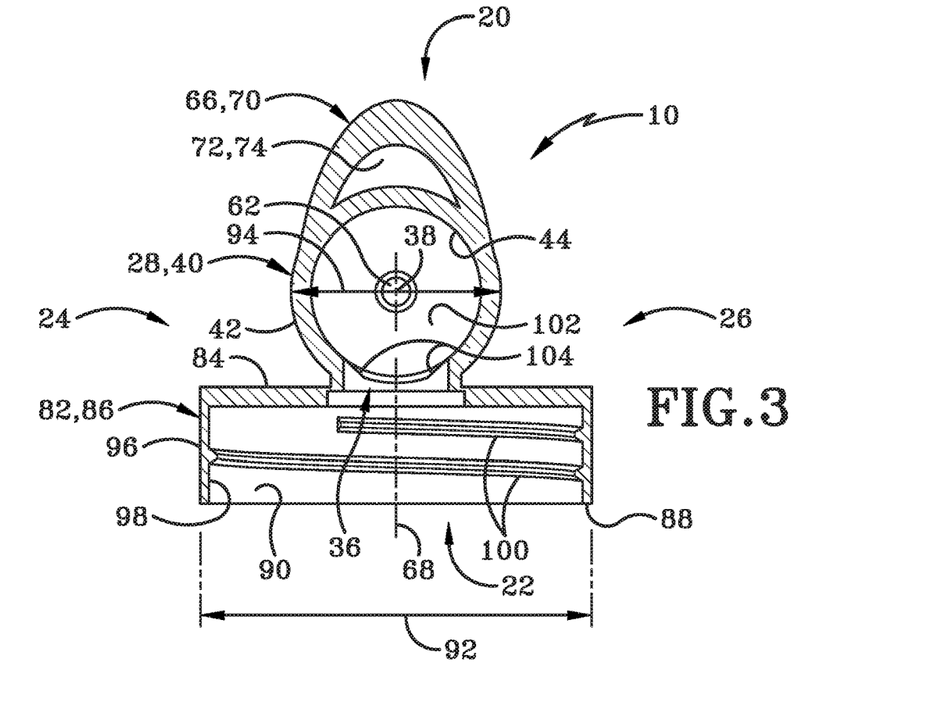

As depicted in FIG. 2 and FIG. 3, a lid 82 is connected adjacent the bottom of the body cylindrical wall 40 of body 28 of adapter 10. The lid 82 includes a generally circular top wall 84 connected with an annular sidewall 86 that extends downwardly from its rigid connection with the circular top wall 84 down to a terminal end 88 defining an opening to a recess 90. Circular wall 84 is generally circular in shape when viewed from above, as best seen in FIG. 2 and includes a circular profile substantially extending in a full circle below a majority of the body cylindrical wall 40 of the body 28. Circular top wall 84 may include an upwardly facing top surface and an opposing downwardly facing bottom surface. Bottom surface of the circular wall may be substantially continuous and is only interrupted by the central edge that defines a portion of the drainage port 36. In one particular embodiment, the lid 82 is integrally formed with the body 28 such that it is part of the adapter 10. However, the lid 82 may also be a distinct component that is rigidly secured to the exterior surface of the body 28, particularly the body cylindrical wall 40 near the bottom end thereof. In one particular embodiment the lid 82 is shaped in an inverted bottle cap configuration, similar to that of a conventional cap commonly found on a sports drink bottle (i.e., a 20 oz. Gatorade® bottle cap).

The diameter of the circular top wall 84 is greater than the transverse width of the body cylindrical wall 40. Stated otherwise, the diameter 92 of the lid 82 is greater than the diameter 94 measured across the longitudinal axis of the body cylindrical wall 40 of the body 28. In one particular embodiment, the diameter of the lid 82 is at least two times greater than the diameter 94 of the body cylindrical sidewall 40 on the body 28. In another particular embodiment, the diameter 92 of the lid 82 is at least three times greater than the diameter 94. The diameter 92 of the lid 82 is smaller than the length associated with the body cylindrical sidewall 40. Stated otherwise, the lid 82 is positioned below the body cylindrical sidewall 40, but terminates short of the tapered collar 46 and the tapered collar 56. Stated otherwise, the lid 82 is disposed between the tapered collar 46 and the tapered collar 56. Additionally, the lid 82 is positioned below the cylindrical extension wall 48 associated with the first inlet 30 and is positioned below the cylindrical extension 58 associated with the outlet 34. In one particular embodiment, the thickness of the annular sidewall 86 measured between the outer surface 96 and the inner surface 98 may be similar to or thinner than the thickness of the body 28 measured between the body cylindrical wall 40, outer surface 42, and inner surface 44.

The annular sidewall 86 may include a convex vertically extending outer surface 96 and an opposing concave vertically extending inner surface 98 having threads 100 extending radially inward towards the vertical axis 68. The threads 100, as will be described in greater detail below are configured to threadably connect with the receptacle 14 to effectuate an air-tight seal between the receptacle and the body 28 to thereby fully assemble the moisture trap assembly 12. Threads 100 or other air tight connection are positioned on the inner circumference of annular sidewall 86 for engaging with the threads or other connection of the receptacle 14, which can be unscrewed and/or separated during draining and cleaning. A vertically aligned length of the annular sidewall 86 is that is less than the diameter 92 of the annular sidewall. Further the vertically aligned length of the annular sidewall 86 is typically less than one inch in length.

As depicted in FIG. 4, the body 28 defines an internal mixing chamber 102 which is in fluid communication with the first inlet 30, the second inlet 32, the outlet 34, and the drainage port 36. The mixing chamber 102 is oriented substantially along the longitudinal axis 38. More particularly, the mixing chamber 102 has a center that is coaxial with the longitudinal axis 38. The mixing chamber 102 is defined by an internal diameter of the body cylindrical wall 40 measured through the longitudinal axis 38 to the opposing side of the inner surface 44. The passageway 52 associated with the first inlet 30 is in open communication and expands in volume in accordance with the shape associated with tapered collar 46. Similarly, the mixing chamber 102 is in fluid communication with the passageway 62 associated with the outlet 34 and tapers downwardly to a narrower volume and a narrower internal diameter at an angle associated with the tapered collar 56.

With continued reference to FIG. 4, the mixing chamber is further defined and bound by a downwardly sloping wall 104 defining a portion of the inner surface 44 adjacent the bottom of the body 28. The sloping wall 104 is angled to effectuate fluid movement that condenses along the inner surface 44 of the mixing chamber 102 to flow towards the drainage port 36. Collectively, the sloping wall 104 and the drainage port 36 define a neck portion of the adapter that leads downwardly to the lid 82. In one particular embodiment, the sloped wall 104 extends in a curved manner downwardly towards the drainage port 36. The sloped wall 104 may begin at a height that is vertically below the longitudinal axis 38. However, other starting points of the sloped wall 104 are envisioned. Further, the sloping wall 104 may be substantially flat or planar in cross section, as opposed to the concave shape in cross section of the inner surface 44. Further, the sloped wall 104 may include other structural features that encourage or effectuate a faster flow of condensate. For example, the sloped wall 104 may be a plurality of sloped walls effectuating or defining a number of channels that guide and direct water or other fluid condensate through the drainage port 36. The drainage port 36 is centered along the vertical axis 68. Thus, centering the drainage port 36 along the central vertical axis 68 offsets the drainage port 36 at an angle relative to the second inlet 32 and the nebulized medicine entering the mixing chamber 102 through holes 80. The drainage port 36 provides open fluid communication between the mixing chamber 102 and the recess 90 defined by the lid 82. As will be described in greater detail below, the sloped wall 104 encourages fluid condensate to flow or trickle through the drainage port 36 and through the recess 90 into the receptacle 14 to be collected and later disposed.

In some instances, an additional seal, such as a gasket, can be included to cover a portion of the drainage port 36 when the receptacle is detached from the lid 82. By doing so, this enables the adapter 10 to operate in a conventional fashion similar to a traditional nebulizer adapter when the receptacle 14 is detached from its connection with the lid 82. In this regard, there may be an actuation member, such as a plunger, provided on the receptacle 14 to move the seal or gasket away from and open the drainage port 36 when the receptacle 14 is threadably attached to the lid 82 via threads 100.

FIG. 5 depicts an operational view in cross-section of the adapter 10 in conjunction with a breathing tube 106, a nebulizer 108, and an outlet tube 110. The tube 106, which may be a respiratory circuit cannula, is inserted into or otherwise connected with the first inlet 30 to establish an open fluid communication between the tube 106 and the mixing chamber 102. Breathing gas, which may be warmed and humidified, is then fed from a source along tube 106 through the first inlet 30 and into the mixing chamber 102. The nebulizer 108 is releasably connected with the second inlet 32 and provides nebulized medicine to move through the passageway 74 and through the plurality of holes 80 into the mixing chamber 102. Notably, the second inlet 32 sized to connect with a wide range of nebulizers including but not limited to an Aeroneb® nebulizer. The nebulized medicine produced in nebulizer 108 mixes with the breathing gas inside mixing chamber 102. During the mixing, it is possible for fluid condensate to collect along the inner surface 44 of the outer cylindrical wall 66 due to the fact that the breathing gas was warmed and humidified. The fluid condensate 112 is directed and guided by the sloping wall 104 towards the center drainage port 36. The fluid condensate 112 may drop, trickle, or otherwise flow and pass through the drainage port 36 and be collected in the receptacle 14 that has been threadably attached to the lid 82. In one particular embodiment, the receptacle 14 may have a diameter measured through its bottom wall that is greater than the diameter of the lid 82. However, it is entirely possible for the diameter of the receptacle 14 to be smaller than the diameter of the lid 82.

In accordance with one aspect of the present disclosure, the adapter 10 enables fluids to be drained therefrom when the nebulized medicine is mixed with the breathing gas entering the mixing chamber through the lumen defined by the first inlet 30. Thus, the first inlet 30 is associated with only a single lumen (i.e., lumen or passageway 52) that fluidly receives breathing gas therethrough. The adapter of the present disclosure operates with and as a single lumen nebulizer systems (i.e., not double lumen systems, such as the first inlet port having double lumens as taught by U.S. PG Pub. 2015/0352299, which may also be referred to as a first inlet double lumen adapter, the entirety of which is hereby incorporated by reference).

In one particular operation of an embodiment, the nebulized medication produced in nebulizer 108 mixes with the breathing gas flowing along tube 106, which may be heated and humidified, that is passed into the mixing chamber 102 through the first inlet 30. The mixed breathing gas and nebulized medication from the second inlet 32 is then flowed out of outlet 34. When the heated and humidified gas is introduced into mixing chamber 102 through the first inlet 30, condensation may occur due to cooling. The condensation is undesirable because condensate could limit the gas flow through the system, present a biologic hazard to the patient, or could potentially flow into a nasal cannula and enter a patient's nasal passage. Condensation is a particular concern for HFT because HFT devices supply breathing gas at a high flow rate. When the breathing gas is pre-heated and humidified for patient comfort, HFT provides a high flow of gas with a high relative humidity and a high temperature. The heating and humidifying of the breathing gas used in HFT is beneficial because high flow rates of dry breathing gas leads to patient discomfort (e.g., due to drying of nasal passages). When heated and humidified gas cools, some of the moisture carried in the breathing gas cannot remain soluble and condenses. With the high flow rate of HFT, there is a substantial amount of moisture in the breathing circuit that could potentially become condensate if the gas cools. Cooling of the heated and humidified gas can occur due to expansion of the gas as it enters the gas mixing chamber. Cooling can also occur due to heat loss to the ambient environment (e.g., radiative cooling at the plastic walls of the adapter).

In one exemplary embodiment, there may be inlet and outlet tubes 106, 110 respectively connected to the adapter 10 (which may sometimes also be referred to as a flow connector unit) and may be about equivalent in size to Vapotherm®, input and output tube dimensions, for example inlet tube diameter of 16.002 mm, congruent with the input tube of the respiratory circuit and outlet tube diameter equivalent of the outer diameter of the cannula, allowing accurate fitment. The outlet tube comprises of the exact diameter in order to prevent disconnection from the HFT including but not limited to Vapotherm®, products.

In addition, the inlet and outlet tubes 106, 110 may be slightly tapered along their respective lengths to ensure a snug fit with the adapter 10 and/or cannula. The inlet and outlet tubes may be linearly shaped with no slanting from the top outer ends toward the center of the lid location with the connecting mesh defined by the plurality of holes 80 at the top opening that fits a wide range of nebulizers 108 including but not limited to the Aeroneb nebulizer.

In another exemplary embodiment, the receptacle 14 comprises a containing volume with a capacity to contain equal to or greater than the condensate calculated by the FDS, hospitals, and collected data. The receptacle may be shaped similar to a cup or a jar having complementary threads formed near the top thereof for effectuating the threaded and hermetic connection with the lid. However, the receptacle may vary in volume and can be secured to the flow connected unit via annular lid. The receptacle is fully secured and does not allow the leakage of gas, water, or medication to leak from within. The collection receptacle may also comprise an actuation member configured to move a seal or gasket that covers a portion of the drainage port 36. The receptacle 14 may additionally define a secondary drainage port at the bottom of the cup allowing the release of accumulated water or fluid condensate from the adapter 10. When ample amount of water or fluid condensate has been accumulated in the collection cup, the cup can be unscrewed, emptied, dried and fitted again to the adapter 10. During detachment of the cup, the air tight seal or gasket covering the drainage port 36 comes to a closed position in order to secure the air or gas flowing through the flow connector thus preventing loss of air of respiratory gas. Once the collection cup is to be securely attached again, the air tight seal will moved by the actuation member carried by the receptacle, thus allowing flow of accumulated water into the collection receptacle during attachment and securing the nebulizer adapter to maintain flow of medication and gas while the receptacle device is disconnected.

An embodiment, the nebulizer adapter 10 with moisture trap assembly 12 used with respiratory apparatuses or other airline circuitry is specifically designed to connect to the input tube of the Vapotherm®, respiratory circuit and the output tube of the cannula by providing congruent dimensions of the body of the nebulizer adapter, while being versatile to fit other HFT and respiratory care devices.

The moisture trap assembly 12 may comprise the exact diameter of the outer cannula dimensions, thus preventing disconnection and leakage of water into the patient respiratory line or other equipment. Moreover, the lid 82 that creates the air tight seal which engages an actuator member when the condensate collection receptacle is removed, thus preventing the loss of gas and medication that is being supplied to the patient. These as well as other advantages of the assembly and modifications within the purview of the present disclosure will be evident to those skilled in the art.

The nebulizer adapter 10 with moisture trap assembly 12 attaches accurately and easily to the Vapotherm® respiratory circuit, and may be attached to other respiratory apparatuses also, in order to reduce the accumulation of water or other fluids in the respiratory apparatus systems, thereby improving patient comfort and safety. The nebulizer adapter 10 with moisture trap provides a less compromised flow of gases, including oxygen, heliox, and precision flow, or other gas by providing an avenue for condensate accumulation while also allowing the uninterrupted passage of gas(es) and medication to the patient.

Although the present disclosure has been described in detail with particular reference to these preferred embodiments, other embodiments can achieve the same results. Variations and modifications of the present disclosure will be obvious to those skilled in the art and it is intended to cover all such modifications and equivalents. The entire disclosures of all references, applications, patents, and publications cited above and/or in the attachments, and of the corresponding application(s), are hereby incorporated by reference.

Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one." The phrase "and/or," as used herein in the specification and in the claims (if at all), should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc. As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures.

An embodiment is an implementation or example of the present disclosure. Reference in the specification to "an embodiment," "one embodiment," "some embodiments," "one particular embodiment," or "other embodiments," or the like, means that a particular feature, structure, or characteristic described in connection with the embodiments is included in at least some embodiments, but not necessarily all embodiments, of the present disclosure. The various appearances "an embodiment," "one embodiment," "some embodiments," "one particular embodiment," or "other embodiments," or the like, are not necessarily all referring to the same embodiments.

If this specification states a component, feature, structure, or characteristic "may", "might", or "could" be included, that particular component, feature, structure, or characteristic is not required to be included. If the specification or claim refers to "a" or "an" element, that does not mean there is only one of the element. If the specification or claims refer to "an additional" element, that does not preclude there being more than one of the additional element.

Additionally, any method of performing the present disclosure may occur in a sequence different than those described herein. Accordingly, no sequence of the method should be read as a limitation unless explicitly stated. It is recognizable that performing some of the steps of the method in an different order could achieve a similar result.

In the foregoing description, certain terms have been used for brevity, clearness, and understanding. No unnecessary limitations are to be implied therefrom beyond the requirement of the prior art because such terms are used for descriptive purposes and are intended to be broadly construed.

Moreover, the description and illustration of various embodiments of the disclosure are examples and the disclosure is not limited to the exact details shown or described.

What is claimed:

1. An adapter for a respiratory line comprising:
a body that defines a first inlet, a second inlet, and an outlet, wherein the first inlet consists of a single lumen that fluidly receives warmed and humidified breathing gas therethrough and the second inlet receives and connects with a nebulizer;
an exterior surface of the body and an interior surface of the body;
a mixing chamber defined by the interior surface of the body, wherein medicine from the nebulizer mixes with the breathing gas inside the mixing chamber and collectively flows outwardly from the body through the outlet;
a drainage port formed in the body in fluid communication with the mixing chamber to drain fluid condensates that condense on the interior surface in the mixing chamber;
a lid connected to the body below the drainage port;
a receptacle removably attached to the lid for collecting fluids flowing out from the mixing chamber through the drainage port;
a receptacle removably attached to the lid for collecting fluids flowing out from the mixing chamber through the drainage port;
a uniform and non-hollow thickness of the bod between the exterior surface and the interior surface to effectuate the adapter as a single lumen adapter and not a first inlet double lumen adapter; and
an annular sidewall on the lid extending downwardly from a circular wall integrally formed with the exterior surface of the body; wherein the annular sidewall is positioned below the mixing chamber and below the second inlet that receives the nebulizer.

2. The adapter of claim 1, further comprising
a central vertical axis, wherein the drainage port s centered along the central vertical axis.

3. The adapter of claim 1, wherein the lid is shaped and formed in an inverted bottle cap configuration.

4. The adapter of claim 1, further comprising:
a screen between the second inlet and the mixing chamber.

5. The adapter of claim 4, wherein the screen is defined by holes formed in a wall of the body between the mixing chamber and the second inlet.

6. The adapter of claim 1, further comprising:
threads on the lid that removably attach the receptacle to the body.

7. The adapter of claim 6, further comprising:
a seal covering the drainage port that is opened in response to the receptacle being threadedly attached to the lid to permit fluid to drain from the mixing chamber through the drainage port and into the receptacle.

8. The adapter of claim 7, further comprising:
an actuation member that opens the seal for the drainage port when the receptacle is attached to the lid.

9. The adapter of claim 1, further comprising: a
central vertical axis extending through the body;
an axis of the second inlet angled in a range from about 15° to about 75° relative to the vertical axis, and wherein a portion of the nebulizer is oriented at a similar angle as the second inlet relative the vertical axis; and
a center of the drainage port aligned along the vertical axis below the second inlet.

10. The adapter of claim 9, further comprising:
a downwardly sloping wall defining a portion of the interior surface of the body in the mixing chamber adjacent the drainage port configured to promote fluid condensate accumulating near the bottom of the mixing chamber to flow outwardly through the drainage port.

11. The adapter of claim 10, further comprising:
an annular sidewall on a lid extending downwardly from a rigid connection adjacent the exterior surface of the body;
a center of the annular sidewall aligned along the vertical axis; and
a diameter of the annular sidewall that is greater than a diameter of the second inlet.

12. The adapter of claim 11, further comprising:
a vertically aligned length of the annular sidewall that is less than the diameter of the annular sidewall.

13. The adapter of claim 11, further comprising:
a vertically aligned length of the annular sidewall that is less than a vertically aligned length of the second inlet.

14. The adapter of claim 11, further comprising:
threads extending radially inward towards the imaginary vertical axis from an inner surface of the annular sidewall; and
complementary threads on a receptacle effectuating the removable attachment between the lid and the receptacle.

15. An adapter for a respiratory line comprising:
a body consisting of a single lumen that fluidly receives warmed and humidified breathing gas therethrough wherein the body has a first end and a second end defining a longitudinal direction therebetween, a top and a bottom defining a vertical direction therebetween, and a first side and a second side defining a transverse direction therebetween, and the body defines a first inlet, a second inlet, and an outlet, wherein the first inlet is associated with the single lumen and the second inlet receives and connects with a nebulizer;
a central vertical axis and a central longitudinal axis, wherein the first inlet and the outlet are centered along the longitudinal axis;
a convex exterior surface of the body and a concave interior surface of the body;
a uniform and non-hollow thickness of the body between the exterior surface and the interior surface to effectuate the adapter as a single lumen adapter;
a cylindrical wall on the body having a length oriented in the longitudinal direction that is greater than its diameter oriented in the vertical direction;
a first tapered collar connected to one end of the cylindrical wall on the body, wherein the first tapered collar is angled downwardly towards the longitudinal axis;
a second tapered collar connected to another end of the cylindrical wall on the body, wherein the second tapered collar is angled downwardly towards the longitudinal axis in a direction opposite that of the first tapered collar, and wherein the second tapered collar is angled at a steeper angle relative to the longitudinal axis than the first tapered collar;

a first cylindrical extension connected with the first tapered collar defining a portion of the first inlet, and the first cylindrical extension having a diameter less than that of the cylindrical wall on the body;

a second cylindrical extension connected with the second tapered collar defining a portion of the outlet, and the second cylindrical extension having a diameter less than that of the cylindrical wall on the body and less than that of the first cylindrical extension;

a mixing chamber defined by the concave interior surface of the body, wherein medicine from the nebulizer mixes with the breathing gas inside the mixing chamber and collective flow outwardly from the body through the outlet along a tube connected with the outlet for inhalation by a patient;

a screen between the second inlet and the mixing chamber, wherein the screen is defined by a plurality of holes formed in the cylindrical wall of the body between the mixing chamber and the second inlet;

an axis of the second inlet angled in a range from about 15° to about 75° relative to the vertical axis, and wherein a portion of the nebulizer is oriented at a similar angle as the second inlet relative the central axis;

a drainage port formed in near the bottom of the body in fluid communication with the mixing chamber to drain fluids that condense on the interior surface when the warmed and humidified breathing gas and medicine are mixed in the mixing chamber, wherein the drainage port is centered along the vertical axis;

a downwardly sloping wall, that is planar in cross section, defining a portion of the interior surface of the body in the mixing chamber adjacent the drainage port configured to promote fluid accumulating near the bottom of the mixing chamber to flow outwardly from the mixing chamber through the drainage port;

a lid connected to the body below the drainage port and centered along the vertical axis, and the lid comprising an annular sidewall extending downwardly from a circular wall integrally formed with the exterior surface of the body and threads on an inner surface of the annular sidewall, wherein the annular sidewall is positioned below the mixing chamber and below the second inlet that receives the nebulizer;

a diameter of the annular sidewall that is greater than a diameter of the cylindrical wall on the body and the diameter of the annular sidewall is less than a length of the cylindrical wall on the body; and a receptacle removably attached to the lid for collecting fluids flowing out from the mixing chamber through the drainage port and complementary threads on the receptacle effectuating the removable attachment between the lid and the receptacle.

* * * * *